(12) United States Patent
Dey et al.

(10) Patent No.: US 11,766,431 B2
(45) Date of Patent: *Sep. 26, 2023

(54) THERAPEUTICAL COMPOSITION CONTAINING APOMORPHINE AS ACTIVE INGREDIENT

(71) Applicant: Britannia Pharmaceuticals Ltd., Reading (GB)

(72) Inventors: Michael Dey, Sandbach (GB); Joel Richard, Mere (FR); Marie-Madeleine Baronnet, Ezy sur Eure (FR); Nathalie Mondoly, Le Chesnay (FR); Laurent Bertocchi, Sylvains les Moulins (FR); Jeremiah Harnett, Gif-sur-Yvette (FR)

(73) Assignee: Britannia Pharmaceuticals Ltd., Reading (GB)

( * ) Notice: Subject to any disclaimer, the term of this patent is extended or adjusted under 35 U.S.C. 154(b) by 213 days.

This patent is subject to a terminal disclaimer.

(21) Appl. No.: 17/245,209

(22) Filed: Apr. 30, 2021

(65) Prior Publication Data

US 2021/0244724 A1 Aug. 12, 2021

Related U.S. Application Data

(63) Continuation of application No. 14/152,000, filed on Jan. 10, 2014, now Pat. No. 11,026,938, which is a continuation of application No. PCT/EP2012/002916, filed on Jul. 11, 2012.

(30) Foreign Application Priority Data

Jul. 11, 2011 (EP) ..................................... 11290320

(51) Int. Cl.
*A61K 31/496* (2006.01)
*A61K 31/473* (2006.01)
*A61K 9/00* (2006.01)

(52) U.S. Cl.
CPC .......... *A61K 31/473* (2013.01); *A61K 9/0019* (2013.01)

(58) Field of Classification Search
CPC .................................................. A61K 31/496
USPC .................................................... 514/253.07
See application file for complete search history.

(56) References Cited

U.S. PATENT DOCUMENTS

| 5,939,094 | A | 8/1999 | Durif et al. |
|---|---|---|---|
| 6,136,818 | A | 10/2000 | Estok |
| 6,193,992 | B1 | 2/2001 | El-Rashidy et al. |
| 6,436,950 | B1 | 8/2002 | Achari et al. |
| 6,939,094 | B2 | 9/2005 | Konishi |
| 8,796,299 | B2 | 8/2014 | Paliwal et al. |
| 11,026,938 | B2 * | 6/2021 | Dey .................. A61P 25/16 |
| 2003/0008878 | A1 | 1/2003 | Cowart et al. |
| 2004/0028613 | A1 | 2/2004 | Quay |
| 2005/0090518 | A1 | 4/2005 | Quay |
| 2008/0171072 | A1 | 7/2008 | Burczynski et al. |
| 2010/0249170 | A1 | 9/2010 | Watts et al. |

FOREIGN PATENT DOCUMENTS

| CN | 101883555 A | 11/2010 |
|---|---|---|
| EP | 1270007 A2 | 1/2003 |
| JP | 5530931 B2 | 6/2014 |
| WO | 9938467 A1 | 8/1999 |
| WO | 9965475 A2 | 12/1999 |
| WO | 02088093 A1 | 11/2002 |
| WO | 03000018 A2 | 1/2003 |
| WO | 03051840 A1 | 6/2003 |
| WO | 2004089988 A2 | 10/2004 |
| WO | 2007134876 A2 | 11/2007 |

OTHER PUBLICATIONS

Wilcox et al. "Stability of Apomorphine in Solutions Containing Ascorbic Acid and Bisulfite and Effects of Antioxidants on Apomorphine-Induced Cage Climbing and Hypothermia in Mice," Journal of Pharmaceutical Sciences vol. 69, No. 3, Aug. 1980.
Pietz et al. "Subcutaneous apomorphine in late stage Parkinson's disease: a long term follow up," J. Neural. Neurosurg. Psychiatry, vol. 65, pp. 709 to 716, 1998.
Kin et al. "Stability of Apomorphine Hydrochloride in Aqueous Sodium Bisulphite Solutions," Prg. Neuro-Psychopharmacol. & Biol. Psychiat., USA, vol. 25, pp. 1461 to 1468, 2001.
Lees et al. "Apomorphine for Parkinson's Disease," Practical Neurology, vol. 2, pp. 280 to 286, 2002.
Waterman et al. "Stabilization of Pharmaceuticals to Oxidative Degradation," Pharm. Dev. Tech. 7(1), pp. 1 to 32, 2002.
Felton (Ed.), excerpts from the pharmaceutical encyclopedia "Remington: Essentials of Pharmaceutics," Pharmaceutical Press, pp. 438,439, and 497, first edition published 2013.
APO-go(R) Ampoules—Summary of Product Characteristics, Britannia Pharmaceuticals Ltd., updated Apr. 1, 2015.
Mehmood et al. Excipients Use in Parenteral and Lyophilized Formulation Development, Open Science Journal of Pharmacy and Pharmacology, vol. 3(3), pp. 19 to 27, 2015.
Product information for apomorphine hydrochloride from Cayman Chemical, Oct. 27, 2016.
Printout from FDA database "Inactive Ingredient Search for Approved Drug Products," link https://www.accessdata.da.gov/scri pts/cder/iig/index.cfm?event=browseByletter.page&Letter= B, accessed Jun. 27, 2019), Year: 2019.

(Continued)

*Primary Examiner* — Raymond J Henley, III
(74) *Attorney, Agent, or Firm* — Tautz & Schuhmacher LLC; Georg Hasselmann

(57) ABSTRACT

A pharmaceutical composition contains apomorphine as the active pharmaceutical ingredient, a water-miscible co-solvent, an antioxidant, and water. The solution has a pH greater than 4. The pharmaceutical composition is suitable for parenteral administration for the treatment of Parkinson's disease. The process for the manufacture of the pharmaceutical composition includes weighing the apomorphine and introducing it into a container with the co-solvent and the antioxidant under agitation until complete dissolution takes place.

18 Claims, 2 Drawing Sheets

(56) References Cited

OTHER PUBLICATIONS

Prescribing Information for APOKYN® (apomorphine hydrochloride injection), US WorldMeds, LLC, 2020.

International Search Report of international application PCT/EP2012/002916 to which this application claims priority, dated Oct. 19, 2012.

\* cited by examiner

THERAPEUTICAL COMPOSITION CONTAINING APOMORPHINE AS ACTIVE INGREDIENT

CROSS REFERENCE TO RELATED APPLICATIONS

This application is a continuation application of U.S. patent application Ser. No. 14/152,000, filed Jan. 10, 2014, now United States patent application publication 2014/0128422 A1, which is a continuation application of international patent application PCT/EP2012/002916, filed Jul. 11, 2012, designating the United States and claiming priority from European patent application 11290320.8, filed Jul. 11, 2011, and the entire content of these applications is incorporated herein by reference.

TECHNICAL FIELD

The present invention relates to a pharmaceutical composition in the form of a solution containing apomorphine as the active pharmaceutical ingredient, and more particularly a pharmaceutical formulation for parenteral administration.

BACKGROUND

Apomorphine is a pharmaceutical active ingredient which is used to reduce "off episodes" in patients with advanced Parkinson's disease. Three solutions of apomorphine are currently marketed: a solution for subcutaneous infusion marketed under the trademark of APO-Go® PFS, a solution for intermittent subcutaneous injection (bolus administration) marketed under the trademark of Apo-Go® ampoules; and a solution of apomorphine for intermittent subcutaneous injection (bolus administration) marketed under the trademark of Apokvn®. These three currently marketed solutions present a pH range of 3.0-4.0.

However, these formulations induce injection site reactions. Therefore the medical precaution for their infusion is to change the injection site every 12 hours and for the bolus administration is to rotate the injection site.

Furthermore, parenteral subcutaneous injection of an active pharmaceutical ingredient (API) formulated in acidic conditions may lead to in situ precipitation and chemical degradation under physiological conditions and pH. Low pH value of the formulation, as well as potential precipitation and degradation of the drug under physiological conditions, may induce local subcutaneous site reactions such as redness, itching, local indurations and nodules which are sore and troublesome. This is typically the case of apomorphine when administered in a subcutaneous (SC) infusion.

To increase the local tolerance of the treatment, the applicant has found a new formulation with a pH close to the physiological pH avoiding in situ precipitation, increasing chemical stability of the formulation and an increased drug concentration allowing the reduction of the injectable volume.

SUMMARY

The object of the present invention is a pharmaceutical composition in the form of a solution comprising
i) apomorphine as the active substance,
ii) a water miscible co-solvent,
iii) an anti-oxidant, in particular an anti-oxidant which is soluble in the mixture consisting of apomorphine and co-solvent and
iv) water,
wherein the pH of the composition is greater than 4.

Unless otherwise indicated the following definitions are set forth to illustrate and define the meaning and scope of the various terms used to describe the invention herein.

The term "co-solvent" as used in the present application refers to a) a solvent or a mixture of solvents which allows the incorporation of the active ingredient in the composition to obtain the required dose in a suitable volume and matches the injectability criteria; or b) a water soluble solid which allows the incorporation of the active ingredient in the composition to obtain the required dose in a suitable volume and matches the injectability criteria.

The term "anti-oxidant" means a pharmaceutically acceptable compound having antioxidant properties in order to prevent oxidative degradation of the active substance and prevent oxidative degradation of the excipients.

The term "surfactant" as used herein refers to a compound or excipient with surface active properties, used mainly in the present formulations to improve the aqueous solubility of the active ingredient, help to protect the active substance against degradation and limit in vitro active ingredient precipitation if co-solvent alone is not sufficient.

The term "pH modifier" as used herein refers to a compound or excipient used mainly to adjust the pH of the formulation.

A composition according to the present invention comprises apomorphine as the active pharmaceutical ingredient (API) (or active substance). The apomorphine API may be in the form of a salt or the free base.

According to the present invention it is preferred that apomorphine is in a salt form. The salts of apomorphine which can be used for the invention are preferably pharmaceutically acceptable salts of organic acids, such as those of acetic, methanesulfonic, arylsulfonic, lactic, citric, tartaric, succinic, glutamic, ascorbic acids, or pharmaceutically acceptable salts of inorganic acids, such as those of hydrochloric, hydrobromic, phosphoric, sulphuric, nitric acids.

According to another preferred embodiment of the invention apomorphine is in the form of the free base.

According to another preferred embodiment of the invention apomorphine is in a salt form, preferably apomorphine is in the form of apomorphine hydrochloride.

In a pharmaceutical composition according to the present invention, the amount of apomorphine as the active ingredient is preferably between 10 to 70 mg/mL. In another preferred embodiment, the amount of apomorphine is between 10 to 65 mg/mL. In another preferred embodiment, the amount of apomorphine as the active ingredient is selected from 10, 20, 30, 40, 50 and 60 mg/mL.

A composition according to the present invention comprises a co-solvent which allows obtaining the required injectability criteria of the pharmaceutical composition. The co-solvent is a solvent or a mixture of solvents or a water soluble solid. The co-solvent is water-miscible (i.e., miscible at least at the concentration of 5% in water at 25° C.) or water-soluble, respectively. It may be selected for instance from an alcohol or a polyol such as diols, triols, mannitol, or a polyether, or a mixture thereof. When the co-solvent is an alcohol, it may be selected for instance from ethanol, isopropanol. When the co-solvent is a polyol, it may be for instance a diol such as propylene glycol, or a triol such as glycerol, or may have more than 3 hydroxyl groups such as mannitol, maltitol or cyclodextrin derivatives such hydroxypropyl-β-cyclodextrin (HPβCD) or sulfobutyl-β-cyclodextrin (SBβCD). When the co-solvent is a polyether, it may be selected for instance from polyoxyethylene glycols or polyoxyethylene glycol derivatives, such as polyoxyethylene glycol 400, Solutol® HS15, Cremophor® ELP.

In a preferred embodiment, the co-solvent is selected from an alcohol or a polyol or a polyether or a mixture thereof, and more preferably from polyols and polyethers or a mixture thereof. In another preferred embodiment, the co-solvent is selected from diols, triols, cyclodextrin derivatives, polyethylene glycols and polyethylene glycol derivatives or a mixture thereof. In a more preferred embodiment, the co-solvent is selected from propylene glycol, glycerol, hydroxypropyl-β-cyclodextrin (HPβCD), sulfobutyl-β-cyclodextrin (SBβCD), polyethylene glycols derivatives or a mixture thereof.

In a preferred embodiment, the amount of co-solvent is between 0.1 to 80% (w:w) of the composition and more preferably between 0.2 to 70% (w:w).

A composition according to the present invention comprises also an antioxidant. Said anti-oxidant is preferably soluble in the mixture consisting of apomorphine and co-solvent(s). It may be selected for instance from acids and their salts, vitamins and derivatives, amino acids, sulfites or phenolic free radical scavengers. When the antioxidant is an acid or a salt thereof, it may be selected for instance from ascorbic acid or its salts such as sodium ascorbate, isoascorbic acid or its salts such as sodium isoascorbate, citric acid or its salts such as sodium citrate, lactic acid, malic acid. When the antioxidant is a vitamin or a vitamin derivative, it may be selected for instance from tocopherol (vitamin E), riboflavine (vitamin B2), tocopherol-PEG-succinate (vitamin derivative), trolox (vitamin derivative). When the antioxidant is an amino acid, it may be selected for instance from cysteine, tryptophane, histidine, selenocysteine, N-acetyl cysteine, taurine, glutathione and glutathione-glutathione. When the antioxidant is a sulfite, it may be selected for instance from sodium sulfite, sodium metabisulfite. When the antioxidant is a phenolic free radical scavenger, it may be selected for instance from butylated hydroxy toluene, butyl hydroxyl anisole, and cinnamic acid.

In a preferred embodiment, the antioxidant is selected from acids and their salts, vitamins and vitamin derivatives, amino acids, sulfites or phenolic free radical scavengers, and preferably from acids and their salts, and sulfites.

In a more preferred embodiment, the antioxidant is selected from ascorbic acid and sodium metabisulfite, and preferably ascorbic acid.

In another preferred embodiment, the antioxidant is ascorbic acid and the ratio (w:w) apomorphine/antioxidant is between 1:0.01 and 1:3.0, preferably between 1:0.03 and 1:2.0, and more preferably between 1:0.05 and 1:0.50.

In another preferred embodiment, the antioxidant is sodium metabisulfite and the ratio (w:w) apomorphine/antioxidant is between 1:0.01 and 1:0.50, preferably between 1:0.03 and 1:0.30, and more preferably between 1:0.09 and 1:0.11. In a more preferred embodiment the antioxidant is sodium metabisulfite and the ratio (w:w) apomorphine/antioxidant is 1:0.10.

A composition according to the present invention may contain other additives usually used in such pharmaceutical compositions such as surfactant, pH modifier.

A composition according to the present invention may contain a surfactant or a mixture thereof. It may be selected for instance from the family of polyoxyethylene sorbitan fatty esters or polyethylene glycol derivatives or poloxamers. When the surfactant is from the family of polyoxyethylene sorbitan fatty esters, it may be selected for instance from polyoxyethylene (80) sorbitan monooleate, polyoxyethylene (20) sorbitan monolaurate, polyoxyethylene (40) sorbitan monopalmitate, polyoxyethylene (60) sorbitan monostearate. When the surfactant is a polyethylene glycol derivative, it may be selected for instance from polyethylene glycol fatty esters such as polyethylene glycol 660 12-hydroxystearate (Solutol® HS 15), or polyethylene glycol castor oil derivatives such as Cremophor® ELP.

In a preferred embodiment, a surfactant is optionally present in the composition. In another preferred embodiment, a surfactant is present in the composition. In a further preferred embodiment, the surfactant present in the composition has a hydrophile-lipophile balance (HLB) between 8 and 20 and more preferably between 12 to 17.

In a preferred embodiment, the surfactant is present in a composition according to the present invention and the surfactant is selected from the family of polyoxyethylene sorbitan fatty esters or polyethylene glycol derivatives or poloxamers. In a more preferred embodiment, the surfactant is selected from polyoxyethylene (80) sorbitan monooleate, polyoxyethylene (20) sorbitan monolaurate, polyethylene glycol castor oil derivatives, and polyethylene glycol derivative and more preferably Cremophor® ELP, or polyethylene glycol 660 12-hydroxystearate (Solutol® HS 15).

In a preferred embodiment, the co-solvent is present in a composition according to the present invention and the apomorphine:co-solvent ratio (w:w) in the composition is between 1:0.1 to 1:40, and preferably between 1:0.2 and 1:30.

The pH of the composition is greater than 4. In a preferred embodiment, the pH of the composition is between 4 and 7, and preferably between 5 and 7. In a more preferred embodiment, the pH of the composition is between 5.5 and 6.5. In a more preferred embodiment, the pH of the composition is selected from 5.8, 5.9, 6.0, 6.1 or 6.2.

In a preferred embodiment, a pH modifier is optionally present in the composition. In another preferred embodiment, a pH modifier is present in the composition. The pH modifier may be selected for instance from sodium hydroxide, sodium bicarbonate, potassium hydroxide, magnesium hydroxide and if necessary acids like hydrochloric acid.

In a preferred embodiment, a pH modifier is present in the composition and it is selected from sodium hydroxide, sodium bicarbonate, potassium hydroxide or magnesium hydroxide.

A pharmaceutical composition according to the present invention is suitable to be administered by parenteral route. In a preferred embodiment, the composition of the present invention is administered by subcutaneous route, and preferably by a subcutaneous infusion.

A pharmaceutical composition according to the present invention shows a low viscosity and is easily administered by the parenteral route through 27 Gauge (G) needle and more preferably through 29 G needle.

A pharmaceutical composition according to the present invention may be useful in the treatment to reduce "off episodes" in patients with advanced Parkinson's disease.

In a preferred embodiment, the composition of the present invention is for use as medicament intended to reduce "off episodes" in patients with advanced Parkinson's disease.

The present invention is further related to the use of a composition according to the invention as injection solution, in particular as injection solution in the treatment of Parkinson's disease.

Furthermore, the invention relates to a process for the preparation of a pharmaceutical composition as described above, said process being defined by the following steps with the order below:

the optional surfactant is weighed followed by the co-solvent in the same container;

the antioxidant is weighed (alone) and dissolved in degassed water;

the antioxidant solution is added to the co-solvent alone or to a mixture of co-solvent with surfactant under agitation;

a quantity of degassed water is added and then the solution is adjusted to around pH 7.5±0.5 and more preferably close to pH 7;

the apomorphine is weighed and introduced into the above solution and agitated until complete dissolution takes place;

the pH is controlled and adjusted if necessary according to the required pH values within the range of pH 4-7, and preferably 5-7, using a pH modifier;

finally, the remaining quantity of degassed water is added to reach the required volume.

The solution is preferably protected from the light. Degassed water is previously obtained by circulating and bubbling dry nitrogen gas in the solution for at least 30 minutes, and the level of oxygen in the solution is monitored using an oxymeter.

Unless otherwise indicated, all technical and scientific terms used herein have the same meaning as commonly understood by a specialist in the domain associated with this invention.

The following examples are presented to illustrate the above procedures and should not be considered as limiting the scope of the invention.

EXPERIMENTAL PART

Example 1: Preparation of Apomorphine Hydrochloride Solution at 40 mg/mL, Propylene Glycol (PG) (45%), Ascorbic Acid (AA) (0.4%), Surfactant Polysorbate (PS80) (0.3%), pH 6

100 mL of apomorphine hydrochloride solution at 40 mg/mL is manufactured according to the following process:

0.3 g of PS80 are weighed in a flask. 45.0 g of PG are added in the flask containing PS80;

in a beaker, 0.4 g of AA or 0.4 g of sodium ascorbate are weighed. 5 g of degassed water for injection (WFI) are added to AA or sodium ascorbate, and AA or sodium ascorbate is dissolved in degassed water under magnetic stirring;

the solution of ascorbic acid is added in the flask containing PG and PS80.

The beaker containing AA solution is rinsed with 5 g of degassed WFI. This rinsing WFI is added to the flask containing PG, PS80 and AA. The solution is homogenised under magnetic stirring;

30 g of degassed WFI are added in the flask containing PS80, PG and AA and the solution is homogenised under magnetic stirring. pH is then adjusted at 7.5±0.5 using a NaOH 1 M solution (to be as close as possible to pH 7.0);

4 g of apomorphine hydrochloride are weighed in a glass vial. Apomorphine hydrochloride is introduced in the flask containing the vehicle adjusted at pH 7.0. The glass vial containing apomorphine hydrochloride is rinsed with 3 g of degassed WFI. The rinsing WFI is added to apomorphine solution. Apomorphine hydrochloride is dissolved under magnetic stirring until complete dissolution of apomorphine hydrochloride;

The pH of the apomorphine solution is then adjusted at pH 6.0±0.2 using a NaOH 0.1 M solution.

The apomorphine hydrochloride solution is maintained under magnetic stirring during introduction of NaOH 0.1 M solution.

Degassed WFI is added to apomorphine hydrochloride solution in order to reach a final weight of 104.8 g of apomorphine hydrochloride solution.

Apomorphine hydrochloride solution is homogenised under magnetic stirring and the final pH is checked.

Example 2: Stability Study of Apomorphine Solutions at 30 mg/mL and 40 mg/mL

Apomorphine content and impurities were analysed using HPLC methods. The characteristics of the HPLC method used for the apomorphine content determination are as follows:

HPLC equipment: Alliance 2695 Waters
Column: YMC ODS-A 5 μm, 46×150 mm, 200 Å
Mobile phase 750 mL buffer: 0.03 M $K_2HPO_4$ pH 3
   250 mL methanol
   0.75 g acid L-tartaric
Solvent for dilution: 0.1% sodium metabisulfite (SM)
   0.1 M HCl
   Sparging with helium for at least 30 minutes
Flow rate: 1 mL/min
Detection: UV at 210 nm
Run time: 20 min
Temperature: Column: ambient—Carousel: 5° C.
Standard solution: 0.05 mg/mL
Injection volume: 25 μL
Retention time: ~8.5 min The characteristics of the HPLC method used for the apomorphine impurities determination are as follows:

HPLC equipment: Alliance 2695 Waters
Column: YMC ODS-A 5 μm, 46×150 mm, 200 Å
Mobile phase: 875 ml buffer: 0.01 M $K_2HPO_4$ pH 3
   125 mL methanol
   0.75 g L-tartaric acid
Solvent for dilution: 0.1% SM
   0.1 M HCl
   Sparging with helium for at least 30 minutes
Flow rate: 1 mL/min
Detection UV at 273 nm
Run time: 110 min
Temperature: Column: ambient—Carousel: 5° C.
Standard solution: 0.0025 mg/ml
Injection volume: 20 μl
Retention time: orthoquinone: 10 min
   impurity A2: ~27 min
   impurity A1: ~ 28 min
   apomorphine: ~35 min The impurity content, which was determined by the area-under-the-curve calculation, is a criteria used to evaluate the stability of the prototypes.

The degree of coloration was assayed using the Eur. Pharmacopoeia colour test.

It has to be noted that the colour grading (from 1 to 7) is inversely proportional to the colour intensity, i.e., 7 means a colourless aqueous solution, while 1 means a highly coloured solution. The materials and the preparations used for this test are colour reference solutions prepared according to Eur. Pharmacopoeia.

Each below formulation (1 to 6) and its supportive stability data are reported in the following Table 1.

Formulation 1: 30 mg/mL apomorphine, 35% PG, 0.2% PS80, 0.3% SM, pH 6.0.

Formulation 2: 30 mg/mL apomorphine, 35% PG, 0.2% PS 80, 0.3% AA, pH 6.0.

Formulation 3: 30 mg/mL apomorphine, 35% PG, 0.3% AA, pH 6.0.

Formulation 4: 40 mg/mL apomorphine, 45% PG, 0.4% AA, pH 6.0.

Formulation 5: 40 mg/mL apomorphine, 45% PG, 0.3% PS 80, 0.4% AA, pH 6.0.

Formulation 6: 30 mg/mL apomorphine, 20% HPβCD, 0.2% PS80, 0.3% SM, pH 6.0. (PG: Propylene glycol; PS 80: Polysorbate 80; HPβCD: Hydroxypropyl β cyclodextrin; SM: sodium metabisulfite; AA: ascorbic acid)

The column headings for the tables are the following:
pH.
degree of coloration noted as "colour"
apomorphine content noted as "Est. content (mg/mL)", since data were obtained without using an apomorphine reference standard; and
total impurities noted as "Total imp. (%)."

TABLE 1

| | | | | | | | | | | | | |
|---|---|---|---|---|---|---|---|---|---|---|---|---|
| | | Test | | | | | | | | | | |
| | | pH | | | Colour | | | Est. Content (mg/mL) | | | Total imp. (%) | |
| Formulation | T0 | T 3 months (25° C.) | T 3 months (40° C.) | T0 | T 3 months (25° C.) | T 3 months (40° C.) | T0 | T 3 months (25° C.) | T 3 months (40° C.) | T0 | T 3 months (25° C.) | T 3 months (40° C.) |
| 1 | 6.0 | 5.7 | 5.5 | <B4 | <B1 | <JV2 | 29.9 | 29.0 | 28.9 | <0.1 | <0.1 | <0.1 |
| 2 | 6.1 | 6.0 | 6.0 | <J4 | <J3 | <JB3 | 29.2 | 30.3 | 30.1 | <0.1 | <0.1 | <0.1 |
| 3 | 6.1 | 6.0 | 6.0 | <J4 | <J3 | <JB3 | 30.4 | 30.2 | 30.1 | <0.1 | <0.1 | <0.1 |
| 4 | 6.0 | 6.1 | 6.1 | <J4 | <J3 | <JB3 | 40.7 | 40.1 | 39.9 | <0.1 | <0.1 | <0.1 |
| 5 | 6.0 | 6.1 | 6.1 | <J4 | <JB3 | <JB3 | 40.5 | 39.7 | 39.9 | <0.1 | <0.1 | <0.1 |
| 6 | 6.0 | 5.8 | 5.7 | GY6 | R3/RY3 | <RY1 | 30.8 | 31.0 | 30.3 | <0.1 | 0.2 | 0.8 |

Example 3: In Vivo Testing

Pharmacokinetic (PK) profile of the selected prototypes were evaluated in rats. Six cannulated rats were used for each prototype. Animals received a subcutaneous injection of the formulation at a dose of 1 mg/kg at a first injection site, a subcutaneous injection of the corresponding vehicle in a second injection site and a subcutaneous injection of saline solution in a third injection site. The injected volumes range between 0.03 to 0.2 mL/kg depending on the concentration of the formulation (0.5 to 30 mg/mL). Blood samples were collected for a 3-hour period. Plasma concentrations were determined by HPLC-MS/MS and PK parameters were calculated.

In order to evaluate the local tolerance of the tested formulations, tissues from the 3 injection sites were collected from each rat and examined by an anatomo-pathologist. A scoring from 0 to 4 (0: no effect, 1: minimal effect, 2: slight effect, 3: moderate effect, 4: severe effect) was attributed for each section and the tolerance was deduced.

The formulations as follows were administered to rats (bolus injection):

Reference: Apo-Go® PFS 5 mg/mL, pH 3.3
Test 1: 29.12 mg/mL apomorphine, 20% SBβCD, 0.3% SM, pH 5.9.
Test 2: 10 mg/mL apomorphine, 0.2% PS 80, 0.1% SM, pH 4.2.
Test 3: 29.36 mg/mL apomorphine, 0.2% PS 80, 30% PG, 0.3% SM, pi 6.0.
Test 4: 29.36 mg/mL apomorphine, 20% HPβCD, 0.2% PS 80, 0.3% SM, pH 5.9.
Test 5: 29.36 mg/mL apomorphine, 0.2% PS 80, 30% PG, 0.3% SM, pH 4.1. (PG: Propylene glycol; PS 80: Polysorbate 80; SBβCD: Sulfobutylether β cyclodextrin; HPβCD: Hydroxypropyl β cyclodextrin; SM: sodium metabisulfite)

These selected prototypes were compared to the reference solution (APO-Go®) regarding the PK profile and the local tolerance.

BRIEF DESCRIPTION OF THE DRAWINGS

The disclosure will now be described with reference to the drawings wherein.

DESCRIPTION OF EXEMPLARY EMBODIMENTS

Figure 1:
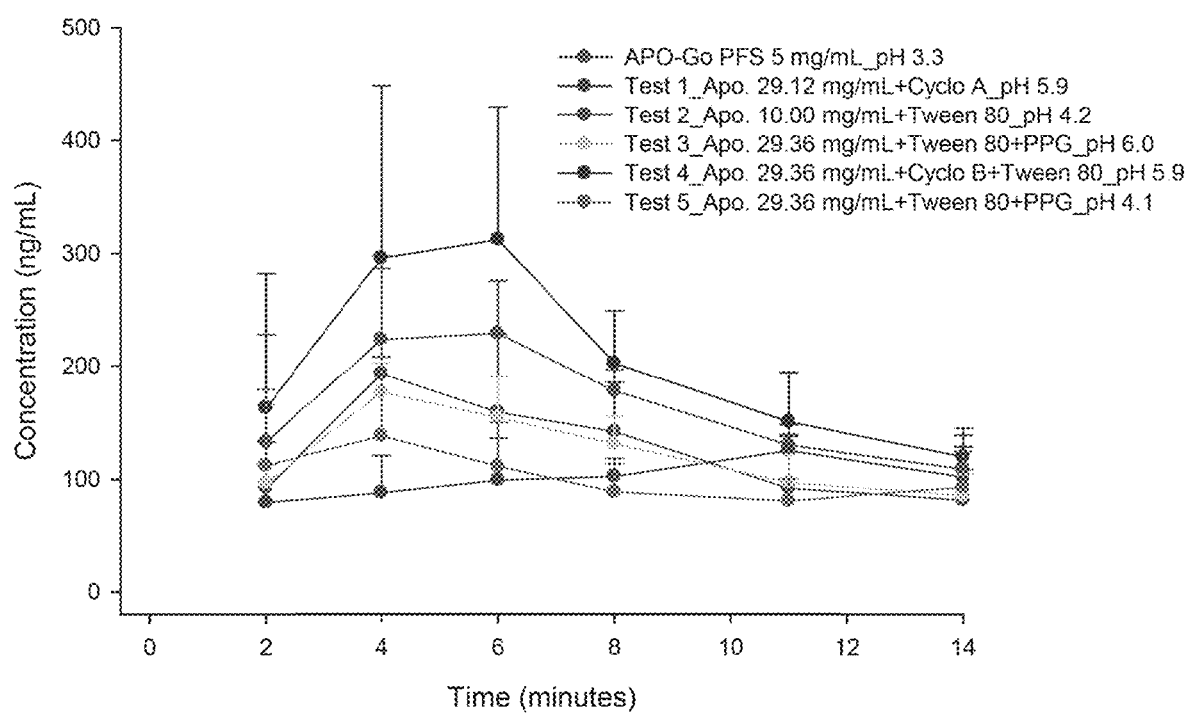
FIG. 1 (details of the absorption phase of tested formulations (1 mg/kg, SC in rats)) shows the plasma profile of apomorphine over the first 14 minutes in order to obtain the PK parameters of the absorption phase.
Figure 2:
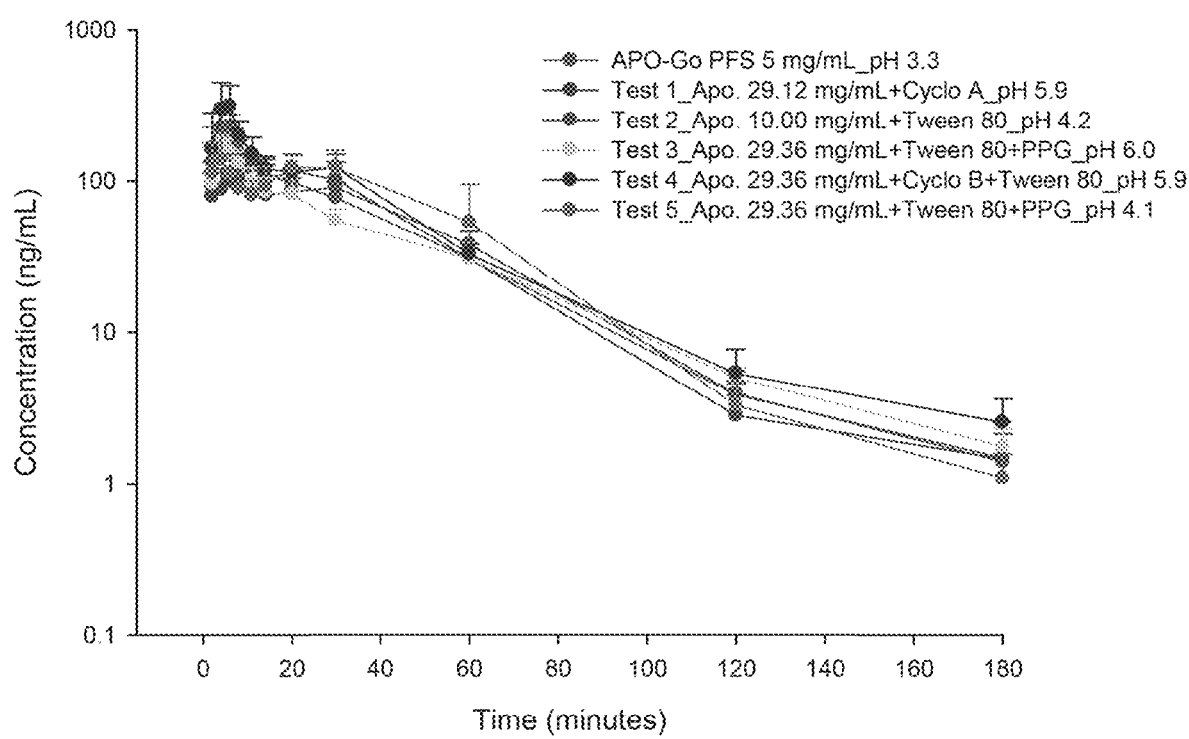
FIG. 2 (PK profiles of tested formulations (1 mg/kg, SC in rats)) shows the overall plasma profile of apomorphine over a 3-hour period.

The PK parameters of these tested formulations in rats (1 mg/kg—SC) are presented in the Table 2.

TABLE 2

| Parameter | APO-go ® | Test 1 | Test 2 | Test 3 | Test 4 | Test 5 |
|---|---|---|---|---|---|---|
| Concentration (mg/mL) | 5.0 | 29.1 | 10.0 | 29.4 | 29.4 | 29.4 |
| pH | 3.3 | 5.9 | 4.2 | 6.0 | 5.9 | 4.1 |
| Cmax (ng/mL) | 242 | 150 | 211 | 191 | 357 | 182 |
| Tmax (min) | 5 | 11 | 4 | 4 | 5 | 9 |
| AUC (ng · h/mL) | 104 | 98 | 99 | 85 | 136 | 113 |
| Bioavailability (%) | Reference | 94 | 95 | 82 | 130 | 108 |

Cmax: maximum value of the apomorphine concentration in the rat serum.
Tmax: time after administration for the apomorphine concentration to reach the Cmax value.
AUC: area under the curve of the PK profile vs time.

The total apomorphine exposure for the above tested formulations was quite similar with regard to the reference, and no major PK differences can be observed for the five test formulations, which are significantly more concentrated than the reference APO-Go® formulation. Consequently all of them show an acceptable profile from a PK point of view.

Example 4: Local Tolerance

The local tolerance results of the tested formulations in rats (1 mg/kg—SC) are presented in Table 3.

TABLE 3

| Parameter | | APO-go ® | Test 1 | Test 2 | Test 3 | Test 4 | Test 5 |
|---|---|---|---|---|---|---|---|
| Concentration (mg/ml) | | 5.0 | 29.1 | 10.0 | 29.4 | 29.4 | 29.4 |
| pH | | 3.3 | 5.9 | 4.2 | 6.0 | 5.9 | 4.1 |
| Tolerance | formulation | 2.7 | 2.4 | 3.7 | 2.3 | 3.0 | 3.2 |
| scoring | placebo | 0.3 | 0.6 | 0.5 | 0.3 | 0.2 | 0.8 |

Note:
tolerance scoring for the saline solution was 0.1.

The same tolerance level as the Apo-Go® reference is observed for the 5 test formulations, which have a concentration from 2 to 6 times higher than the reference (from 10 to 30 mg/mL for the test formulations vs. 5 mg/mL for the reference).

Thus, using a formulation according to the present invention, patients will be able to receive a better treatment based on a 6-fold lower injection volume, a formulation at a more physiologically acceptable pH and a formulation that tends to be more tolerated than the APO-Go® reference.

Example 5: 14-Day Subcutaneous Infusion In Vivo Testing

PK profile of the selected prototypes were evaluated in rats. Subcutaneous micropumps were implanted in 6 rats for each prototype. Micropumps were implanted subcutaneously in the lumbar region for continuous infusion in the scapular region. Animals received a subcutaneous infusion of the formulation at a dose of 6 mg/kg/day (0.3 mg/kg/hour) of the appropriate apomorphine formulations to animals over a 20 h period/day for 14 days. Blood samples were collected at the following time point:

Day 1 at 0 h, 6 h post Start of Infusion and 20 h post Start of Infusion (SOI),
Day 7 20 h post Start of Infusion (SOI),
Day 14 at 0 h, 20 h post Start of Infusion (SOI).

Plasma concentrations were determined by HPLC-ESI-MS/MS method and PK parameters were calculated.

In order to evaluate the local tolerance of the tested formulations, tissue from the injection site was collected from each rat and examined by an anatomo-pathologist. A scoring from 0 to 4 (0: no effect, 1: minimal effect, 2: slight effect, 3: moderate effect, 4: severe effect) was attributed for each section and the tolerance was deduced.

The formulations as follows were administered to rats (infusion injection):

Test 1 (reference): Apo-Go® PFS 5 mg/mL, pH 3.3
Test 2: 30 mg/mL apomorphine, 35% PG, 0.2% PS80, 0.3% SM, pH 6.0.
Test 3: 30 mg/mL apomorphine, 35% PG, 0.2% PS 80, 0.3% AA, pH 5.8.
Test 4: 30 mg/mL apomorphine, 35% PG, 0.3% AA, pH 5.9.
Test 5: 40 mg/mL apomorphine, 45% PG, 0.4% AA, pH 5.9.
Test 6: 40 mg/mL apomorphine, 45% PG, 0.3% PS 80, 0.4% AA, pH 5.9. (PG: Propylene glycol; PS 80: Polysorbate 80; SM: sodium metabisulfite; AA: ascorbic acid)

These selected prototypes were compared to the reference solution (APO-Go®, Test 1) regarding the PK profile and the local tolerance.

The PK parameters of these tested formulations in rats (6 mg/kg/day—SC continuous infusion) after day 1, 7 and 14 are presented in the Table 4.

TABLE 4

| Parameter | Test 1 (Reference) | Test 2 | Test 3 | Test 4 | Test 5 | Test 6 |
|---|---|---|---|---|---|---|
| Concentration (mg/mL) | 4.58 | 28.9 | 29.6 | 30.4 | 39.5 | 37.2 |
| pH | 3.3 | 6.0 | 5.8 | 5.9 | 5.9 | 5.9 |
| $C_{maxss}$ (ng/ml) on day 1 | 12.95 | 17.16 | 13.43 | 12.19 | 13.51 | 10.02 |
| $C_{maxss}$ (ng/ml) on day 7 | 10.35 | 13.01 | 9.79 | 11.53 | 7.17 | 9.25 |
| $C_{maxss}$ (ng/ml) on day 14 | 15.21 | 9.68 | 8.73 | 7.30 | 2.76 | 9.54 |

$C_{maxss}$: is the maximum concentration of apomorphine in plasma at steady-state conditions. The value on day 1 was calculated as the mean of all concentration values obtained at 6 and 20 hours Post-start of infusion (SOI) (2 sample time points). At the 7$^{th}$ infusion day, $C_{maxss}$ is the mean of all concentration values at day 7 (single sample time point). At the 14$^{th}$ infusion day, is the mean of all concentration values at 20 h Post-SOI, i.e., at the end of infusion (EOI) (single sample time point).

Apomorphine exposure data of above tested formulations were similar with regard to the reference.

The PK parameters of these tested formulations in rats (6 mg/kg/day—SC continuous infusion) on day 14 are presented in the Table 5.

TABLE 5

| Parameter | Test 1 (Reference) | Test 2 | Test 3 | Test 4 | Test 5 | Test 6 |
|---|---|---|---|---|---|---|
| Concentration (mg/mL) | 4.58 | 28.9 | 29.6 | 30.4 | 39.5 | 37.2 |
| pH | 3.3 | 6.0 | 5.8 | 5.9 | 5.9 | 5.9 |
| $C_{maxss}$ (ng/ml) on day 14 | 15.2 | 9.68 | 8.73 | 7.30 | 2.76 | 9.54 |
| AUC (ng · h/ml) | 277 | 210 | 178 | 183 | 75 | 173 |

$C_{maxss}$ corresponds to the mean concentration obtained after 20 h Post SOI

No major PK differences can be observed for the five test formulations. Consequently all of the test formulations show an acceptable profile from a PK point of view.

Example 6: Local Tolerance in the 14-Day Subcutaneous Infusion Experiment

The local tolerance of the tested formulations in subcutaneous infusion over 20 h/day in rats at 6 mg/kg/d are presented in the Table 6. The tolerance scoring was established at the 14$^{th}$ day of infusion, i.e., at the EOI.

TABLE 6

| Parameter | Test 1 (Reference) | Test 2 | Test 3 | Test 4 | Test 5 | Test 6 |
|---|---|---|---|---|---|---|
| Concentration (mg/mL) | 4.58 | 28.9 | 29.6 | 30.4 | 39.5 | 37.2 |
| pH | 3.3 | 6.0 | 5.8 | 5.9 | 5.9 | 5.9 |
| Tolerance scoring | 3.0 | 2.8 | 2.3 | 2.7 | 2.4 | 2.6 |

The same tolerance level than the Apo-Go® reference (Test 1) was obtained with the test formulations that show a 6 to 8 times higher concentration.

Thus, using a formulation according to the present invention, patients will be able to receive a better treatment based on a 6 to 8 times lower injection volume, a formulation at a more physiologically acceptable pH and a formulation that tends to be more tolerated than the APO-Go® reference.

It is understood that the foregoing description is that of the preferred embodiments of the invention and that various changes and modifications may be made thereto without departing from the spirit and scope of the invention as defined in the appended claims.

The invention claimed is:

1. A pharmaceutical composition in the form of a solution comprising:
   i) apomorphine as the active substance;
   ii) a water miscible co-solvent;
   iii) an anti-oxidant; and
   iv) water,
wherein a pH of the composition is greater than 4.

2. The composition according to claim 1, wherein an amount of the active substance is between about 10 to 70 mg/ml.

3. The composition according to claim 1, wherein an amount of the water miscible co-solvent is between 0.1 to 80% (w/w) of the composition.

4. The composition according to claim 1, wherein the co-solvent is selected from the group consisting of an alcohol, a polyol, and a polyether or a mixture thereof.

5. The composition according to claim 1, wherein the co-solvent is selected from the group consisting of a diol, a triol, a cyclodextrin derivative, a polyethylene glycol, and a polyethylene glycol derivative or a mixture thereof.

6. The composition according to claim 1, wherein the antioxidant is selected from the group consisting of an acid, a salt of the acid, a vitamin, a vitamin derivative, an amino acid, a sulfite, and a phenolic free radical scavenger or a mixture thereof.

7. The composition according to claim 1, wherein the antioxidant is selected from the group consisting of ascorbic acid and sodium metabisulfite or a mixture thereof.

8. The composition according to claim 1, wherein the pharmaceutical composition further comprises a surfactant.

9. The composition according to claim 8, wherein the surfactant has a hydrophile-lipophile balance (HLB) between 8 and 20.

10. The composition of claim 8, wherein the surfactant is selected from the group consisting of a polyoxyethylene sorbitan fatty ester, a polyethylene glycol derivative, and a poloxamers or a mixture thereof.

11. The composition according to claim 1, wherein an apomorphine: co-solvent ratio (w:w) is between 1:0.1 to 1:40.

12. The composition according to claim 1, wherein the pH of the composition is between 4 and 7.

13. The composition according to claim 1, wherein the pharmaceutical composition further comprises a pH modifier.

14. The composition according to claim 13, wherein the pH modifier is selected from the group consisting of sodium hydroxide, sodium bicarbonate, potassium hydroxide, magnesium hydroxide, and hydrochloric acid, or a mixture thereof.

15. A method of administering the composition according to claim 1 to a patient in need thereof, wherein the composition is administered by parenteral route.

16. A method of reducing "off episodes" in a patient with advanced Parkinson's disease comprising administering the composition according to claim 1 to the patient.

17. An injection solution for the treatment of Parkinson's disease comprising the composition according to claim 1.

18. A process for the manufacture of a composition according to claim 1, the process comprising:
i) providing a first container;
ii) optionally, weighing a surfactant in the first container;
iii) adding the co-solvent to the first container;
iv) weighing the antioxidant in a second container and dissolving the antioxidant in degassed water to obtain an antioxidant solution;
v) adding the antioxidant solution to the first container under agitation;
vi) adding a degassed water to the first container and adjusting the pH to about 7.5±0.5;
vii) weighing the apomorphine and introducing the apomorphine to the first container under agitation until complete dissolution takes place;
viii) controlling the pH of the solution in the first container within the range of 4 to 7 by adding a pH modifier as necessary to maintain the pH within the range; and
adding a remaining quantity of degassed water to reach a predetermined volume of the solution.

* * * * *